(12) United States Patent
Li et al.

(10) Patent No.: US 11,723,315 B2
(45) Date of Patent: *Aug. 15, 2023

(54) LIGHT REGULATION METHOD FOR PROMOTING ACCUMULATION OF CANNABINOID SUBSTANCES

(71) Applicant: Fujian Sanan Sino-Science Photobiotech Co., Ltd., Quanzhou (CN)

(72) Inventors: Shaohua Li, Quanzhou (CN); Yang Li, Quanzhou (CN); Yiqun Chen, Quanzhou (CN); Guojie Liu, Quanzhou (CN); Desheng Su, Quanzhou (CN)

(73) Assignee: FUJIAN SANAN SINO-SCIENCE PHOTOBIOTECH CO., LTD., Quanzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/384,717

(22) Filed: Jul. 24, 2021

(65) Prior Publication Data
US 2021/0386024 A1 Dec. 16, 2021

Related U.S. Application Data

(63) Continuation-in-part of application No. PCT/CN2019/106427, filed on Sep. 18, 2019.

(51) Int. Cl.
| | |
|---|---|
| A01H 3/02 | (2006.01) |
| A01G 7/04 | (2006.01) |
| A01G 7/06 | (2006.01) |
| A01G 9/20 | (2006.01) |
| A01G 22/00 | (2018.01) |
| F21V 9/30 | (2018.01) |
| A01G 22/15 | (2018.01) |
| A01H 6/28 | (2018.01) |
| F21Y 115/10 | (2016.01) |
| F21Y 113/17 | (2016.01) |

(52) U.S. Cl.
CPC .............. *A01G 7/045* (2013.01); *A01G 7/06* (2013.01); *A01G 9/20* (2013.01); *A01G 22/00* (2018.02); *A01G 22/15* (2018.02); *A01H 3/02* (2013.01); *A01H 6/28* (2018.05); *F21V 9/30* (2018.02); *F21Y 2113/17* (2016.08); *F21Y 2115/10* (2016.08)

(58) Field of Classification Search
CPC .......... A01G 7/045; A01H 3/02; A01H 1/101; A01H 5/02; A01H 5/12; A01H 6/28
See application file for complete search history.

(56) References Cited

PUBLICATIONS

Bilodeau, S. et al. "An Update on Plant Photobiology and Implications for Cannabis Production," Frontiers in Plant Science, vol. pp. 1-15, Mar. 2019.*
Runkle, E. "Growing Plants with Green Light," Greenhouse Product News, Jun. 2017, (Retrieved form the Internet on Dec. 20, 2021—https://gpnmag.com/article/growing-plants-with-green-light/).*
Singh, D. et al. "LEDs for energy efficient greenhouse lighting," Renewable and Sustainable Energy Reviews; 49(2015):139-147.*
Hawley et al. "Improving Cannabis Bud Quality and Yield with Subcanopy Lighting," HortScience 53(11):1593-1599, 2018.*
Kim, H. et al. "Green-light Supplementation for Enhanced Lettuce Growth under Red-Blue-light-emitting Diodes," HortScience 39(7): 1617-1622, 2004.*
Rechner et al. "Can narrow-bandwidth light from UV-A to green alter secondary plant metabolism and increase *Brassica* plant defenses against aphids?", Plos One, Nov. 30, 2017, pp. 1-20.*
ISR of PCT/CN2019/106427.
Magagnini, G. et al. "The Effect of Light Spectrum on the Morphology and Cannabinoid Content of *Cannabis sativa* L.," Medical Cannabis Cannabinoids, 2018, vol. 1, No. 1, pp. 19-17.
Paul, G. M. et al., "Effect of Light Quality on Cannabinoid Content of *Cannabis sativa* L. (Cannabaceae)," Bot.Gaz., 1983, 144(1): 43-48.
Hawley, D., "The influence of spectral quality of light on plant secondary metabolism and photosynthetic acclimation to light quality," Ph.D. dissertation, The University of Guelph., 2018, pp. 1-163.
Bilodeau, S.E. et al., "An Update on Plant Photobiology and Implications for Cannabis Production," Front. Plant Sci., 2019, vol. 10, Article 296; pp. 1-15.
Hawley, D. et al., "Improving Cannabis Bud Quality and Yield with Subcanopy Lighting," Hortscience, 2018, 53(11): 5193-1599.
Lalge et al., "The Effects of Red, Blue and White Light on the Growth and Development of *Cannabis sativa* L.," Mendel Net, 2017, 24: 646-651, Brno Czech Republic.
Kim Hyeon-Hye et al., "Green-light Supplementation for Enhanced Lettuce Growth under Red- and Blue-light-emitting Diodes," HortScience, 2004, 39(7): 1617-1622.
Zhang et al., "Green light signaling and adaptive response," Plant Signaling & Behavior, 2012, 7(1):1-4.

* cited by examiner

*Primary Examiner* — Susan McCormick Ewoldt

(57) ABSTRACT

A method for promoting the accumulation of cannabinoid substances is disclosed. The method comprises the step of adding an irradiation of green light, which has a peak wavelength at 505-526 nm, into the indoor growing environment of cannabis to improve the levels of tetrahydrocannabinol (THC) and cannabidiol (CBD), cannabinoid substances in cannabis. While maintaining the light intensity and other growth conditions, the yields and/or levels of THC and CBD, cannabinoid substances in cannabis, can be increased by up to 21.35%.

3 Claims, 3 Drawing Sheets

LIGHT REGULATION METHOD FOR PROMOTING ACCUMULATION OF CANNABINOID SUBSTANCES

CROSS REFERENCE TO RELATED APPLICATIONS

This application is a continuation in part of PCT patent Application No. PCT/CN2019/106427, filed on Sep. 18, 2019, entitled "Light Regulation Method for Promoting Accumulation of Secondary Metabolites in Cannabis Plants", which claims priority of U.S. patent application Ser. No. 16/446,602, filed on Jun. 19, 2019, in the USPTO, the entire content of which are hereby incorporated by reference in their entireties.

TECHNICAL FIELD

The subject matter herein relates to a technical filed of medicinal plants, and in particularly relates to a method for promoting accumulation of cannabinoid substances.

BACKGROUND

Cannabis (*Cannabis sativa* L.) is an annual erect herb. The main active ingredient in cannabis plants is cannabinoids. Currently, over 70 kinds of natural cannabinoids are found, which are mainly used in some nervous system diseases, such as multiple sclerosis, motor neuropathy, chronic intractable pain, a drug-induced vomiting. Tetrahydrocannabinol (THC) and cannabidiol (CBD) are the main active ingredients. The level of CBD is a key medicinal quality indicator of industrial hemp mosaic. As a non-psychoactive compound, CBD has excellent tolerance and above-average safety, and is widely used in the field of medical research. CBD exerts analgesic and anti-inflammatory effects through dual inhibition of cyclooxygenase and lipoxygenase. It also has potential medical value in the treatment of schizophrenia, Alzheimer's disease and epilepsy. It also has a good intervention effect for drug-induced mental dependence such as morphine, cocaine, alcohol or the like. THC is a psychoactive cannabinoid. It is usually administered orally or inhaled. After being absorbed, it circulates through the blood to various organs and tissues, thereby exerting effects including analgesia, anti-inflammatory, immune regulation, anti-cancer, etc. THC and CBD levels are one of the important indicators of high-quality medicinal cannabis. Medicinal cannabis with high level of THC and CBD has higher medicinal value and economic benefits in the cannabinoid extraction and processing industry. Therefore, the cannabis cultivation and regulation technology for obtaining high levels of medicinal ingredients has important application value. Accordingly, the cultivation technology of medicinal cannabis plants with high levels CBD and THC has become a difficult point that needs to be solved urgently.

Indoor cultivation of cannabis can obtain plant raw materials with stable level and yield of medicinal ingredients in full years without being affected by seasons, because the indoor cultivation of cannabis has stable environmental factors including light, temperature, humidity, nutrition and the like required for growth. Light is one of the most relevant environmental factors influencing plant behavior. It is not only the basic energy source for photosynthesis, but also an important regulator of plant growth and development, which plays a significant role in plants' morphogenesis, reproductive development, and regulation of secondary metabolites. Cannabis is a light-loving and short-day plant, which is sensitive to light. It is an important technical means to improve the secondary metabolites for medicinal components by adjusting the light quality ratio of the light environment in the growth of cannabis. The way to adjust the light quality ratio of the light environment is feasible and simple for implementation. It will become an effective technology for producing medicinal cannabis with high levels of CBD and THC and provide a reliable way to provide high-quality raw materials for producing cannabinoid.

At present, high-pressure sodium lamps (HPS), metal halide lamps (MH), and light-emitting diode lights (LED) are mainly used to provide a light environment for indoor cannabis cultivation. HPS and MH are limited by their spectral design, and the achievable spectral energy distribution is limited. LED lights have the characteristics of narrow half-height and flexible spectral design, which have been widely studied. It has become an important research goal of high-quality and high-efficiency cultivation and production of medical cannabis to explore the cultivation methods for promoting accumulation of CBD and TCH. However, in the LED light spectrum matching method that promotes accumulation of secondary metabolites in plants, it has not yet disclosed how to promote the indoor cultivation and growth of cannabis plants to achieve a better effect of promoting accumulation of levels of CBD and TCH, the secondary metabolites in cannabis.

SUMMARY

With respect to the background, one object of the present disclosure is to provide a method for promoting accumulation of CBD level in cannabis by adjusting a growing environment of cannabis.

Specifically, the object of the present disclosure is achieved by the following embodiments.

A method for promoting accumulation of CBD, secondary metabolites in cannabis. The method is achieved by adding an irradiation of green light having a peak wavelength at 505-526 nm in an indoor growing environment of cannabis to increase the accumulation of CBD level and yield in cannabis.

In some embodiments, the step of adding the irradiation of green light having a peak wavelength at 505-526 nm comprises a combined irradiation with other wavelength bands or independent irradiation.

In some embodiments, in the combined irradiation with other wavelength bands, a ratio of the photon number of the green light to the photon number of the entire light source does not exceed 50%.

In some embodiments, the light source used in the indoor growing environment of cannabis is a LED light source.

In some embodiments, the LED light source is composed of 11.6-16.4% blue light, 46.4-65.6% red light, and 18-42% green light.

In some embodiments, the blue light has a peak wavelength at 440-460 nm, the red light has a peak wavelength at 655-690 nm, and the green light has a peak wavelength at 505-526 nm.

In some embodiments, the peak wavelength of the green light lies at 515-523 nm.

In some embodiments, the light source comprises 18-42% green light.

In some embodiments, the light source comprises 31-37% green light.

In some embodiments, a ratio of the photon number of the blue light to the photon number of the red light is 1:4.

In some embodiments, the LED light source is realized directly by a LED chip or by using the LED chip to excite a phosphor material.

In some embodiments, an initial light intensity is 80 $\mu mol/m^2s$, a maximum light intensity is 1000 $\mu mol/m^2s$, and a photoperiod is 10-16 h/d.

Compared with the prior art, the present disclosure has the following advantages.

The present disclosure provides a method for promoting accumulation of THC and CBD, secondary metabolites in cannabis. By introducing the irradiation of green light, which has a peak wavelength at 505-526 nm, into the indoor growing environment of cannabis, and maintaining the light intensity and other growth conditions, the yields and/or levels of THC and CBD, the secondary metabolites n cannabis, can be effectively promoted by at least 21.35%.

DETAILED DESCRIPTION OF THE INVENTION

The present disclosure will be further described in detail below with reference to the drawings and specific embodiments, in order to better understand the objective, the technical solution and the advantage of the present disclosure. It should be understood that the specific embodiments described herein are merely illustrative and are not intended to limit the scope of the disclosure.

Figure 1:
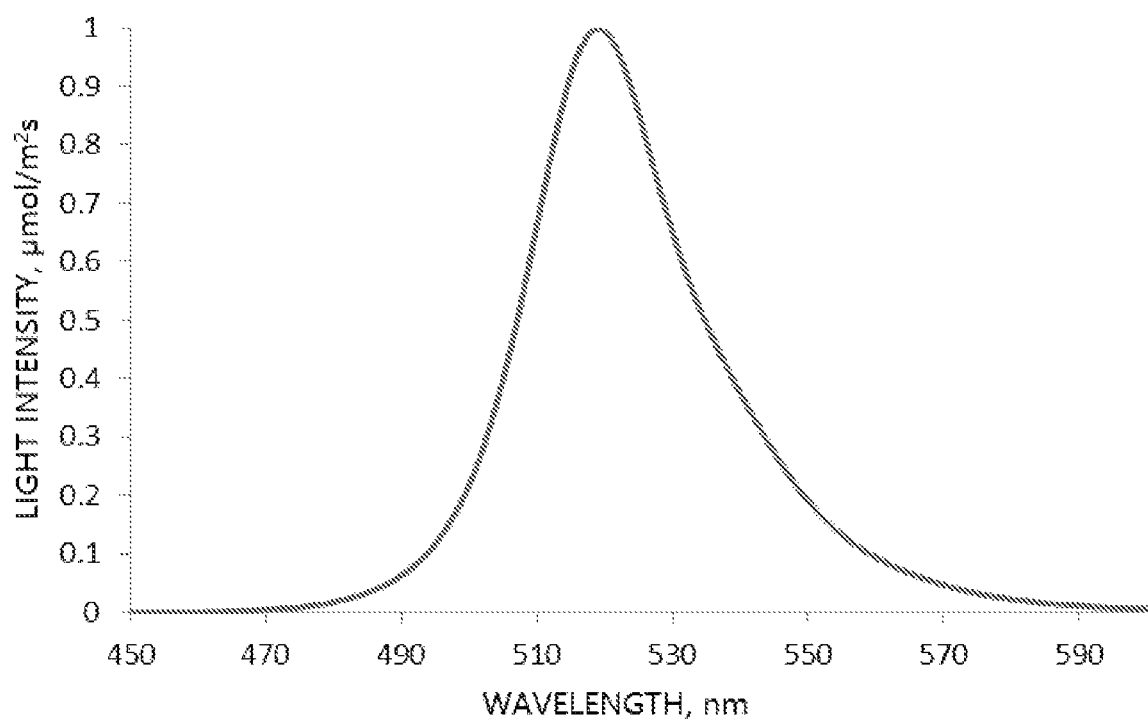
FIG. 1 is a spectral distribution diagram from a LED light source which is realized directly by a LED chip according to the present disclosure.
Figure 2:
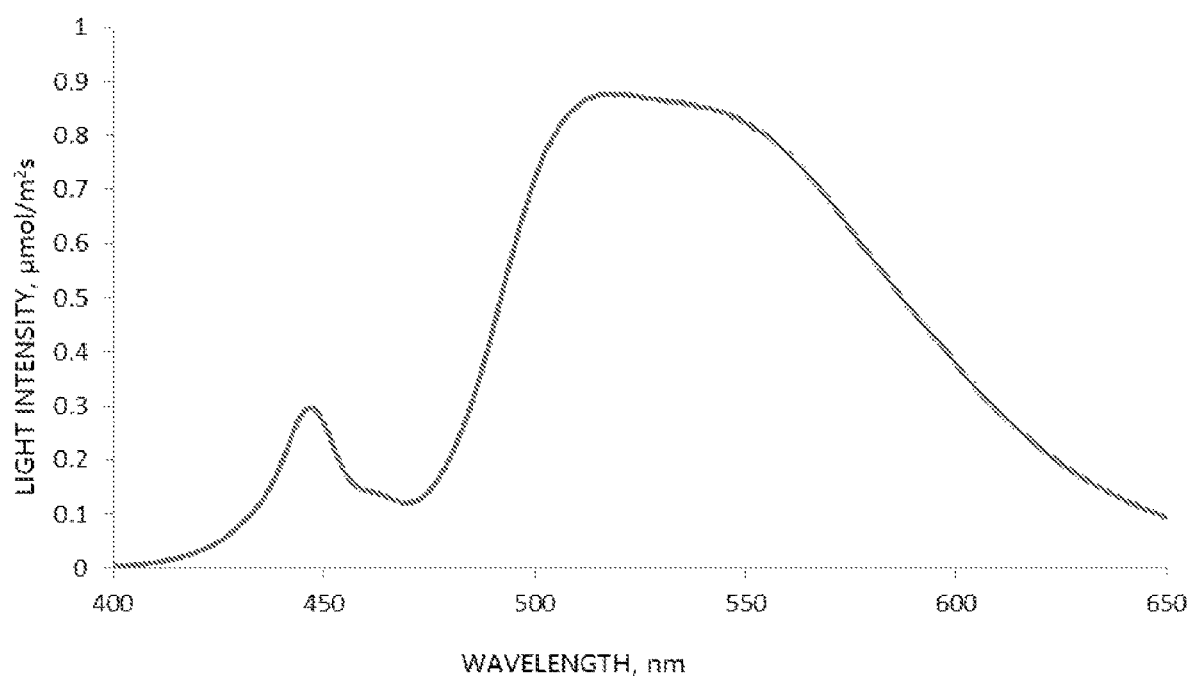
FIG. 2 is a spectral distribution diagram from a LED light source which is realized by using the LED chip to excite a phosphor material according to the present disclosure.
Figure 3:
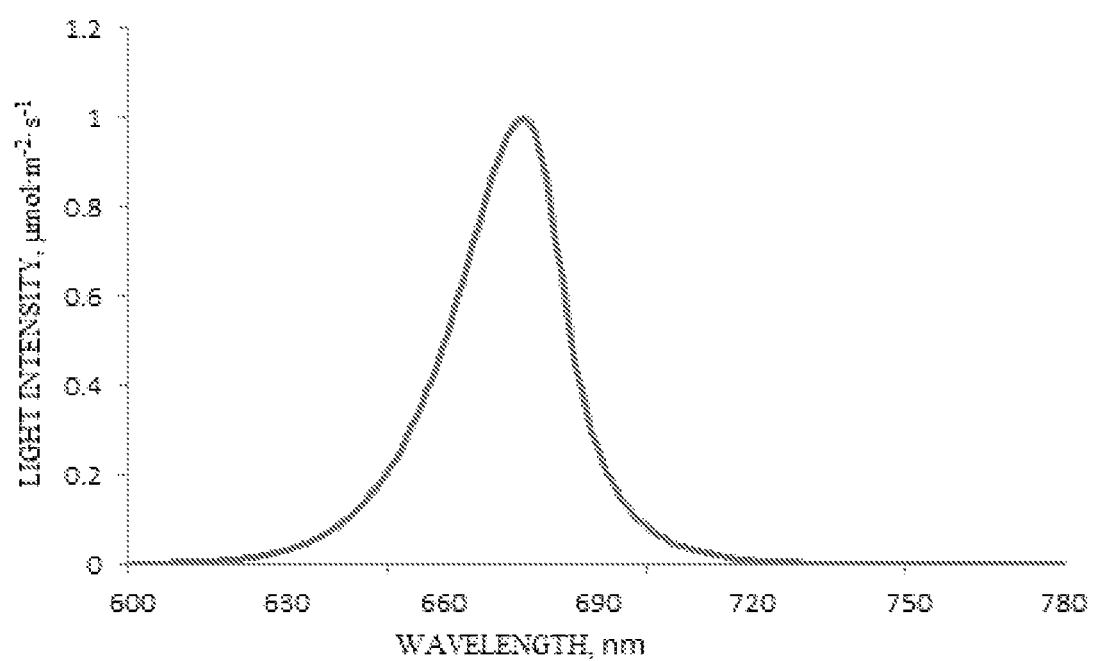

In the early stage of treatment to cannabis seedling, top branches of strong cannabis mother plant are selected as stem cuttings for plant cutting, or cannabis seeds are selected for sowing. The seedling stage is about 2 weeks. The cannabis seedlings with good rooting conditions are transplanted into the substrate or rock wool for the vegetative growth phase (the vegetative growth stage is about 4 weeks). Each rock wool block has 1 plant, and a density for the transplanted cannabis seedlings is 9 plants/m². The plant is topped when the plant is about 20 cm high for triggering the growth of side branches. After the vegetative growth stage is finished, the plant is moved to the flower promotion stage for flower promotion treatment. The planting density of the plant in the flower promotion stage is 4-6 plants/m². A distinguishment to the male and female flowers is required. The male flowers will be removed, and the female plants will be cultivated. The cultivation environment is set to have a day and night temperature at 24-26° C./21-22° C., humidity at 60-70%, $CO_2$ concentration at 10000 ppm. Throughout the growth process, the LED light source directly realized by the LED chip is an artificial light source. The spectrum distribution diagram directly realized by the LED chip is shown in FIG. 1. The LED light source as shown provides a light environment for the growth of cannabis. An initial light intensity is set to 80-100 $\mu mol/m^2s$. As the plant height increases, the light intensity may reach 500-1000 $\mu mol/m^2s$ in the late stage, and the photoperiod is 10-16 h/d. After 7-9 weeks of growth at the flowering stage, the accumulation of CBD and THC level, the cannabinoid substances in plants, would be promoted.

Embodiment 1

Top branches of strong cannabis mother plant are selected as stem cuttings for plant cutting. After the plant cutting is finished (the plant cutting stage is about 2 weeks), the cannabis seedlings with good rooting conditions are transplanted into the rock wool or the substrate for the vegetative growth phase (the vegetative growth stage is about 4 weeks). Each rock wool block has 1 plant, and a density for the transplanted cannabis seedlings is 9 plants/m². The plant is topped when the plant is about 20 cm high for triggering the growth of side branches. After the vegetative growth stage is finished, the plant is moved to the flower promotion stage for flower promotion treatment. The planting density of the plant in the flower promotion stage is 4 plants/m². A distinguishment to the male and female flowers is required. The male flowers are removed, and the female plants is cultivated as before. The cultivation environment is set to have a day and night temperature at 24-26° C./21-22° C., humidity at 60-70%, $CO_2$ concentration at 10000 ppm. Throughout the growth process, the LED light source is used to provide a light environment for the growth of the plant. An initial light intensity is set to 100 $\mu mol/m^2s$. As the plant height increases, the light intensity reaches 550 $\mu mol/m^2s$ in the late stage, and the photoperiod is 12 h/d. Blue LED light source with a peak wavelength at 445 nm, yellow-green LED light source with a peak wavelength at 545 nm, and yellow-green LED light source with a peak wavelength 571 nm are provided as control examples 1-3, respectively. Green LED light sources with peak wavelengths at 505 nm, 515 nm, 523 nm, 526 nm are provided as experimental examples 1-4, respectively. When harvesting, the CBD and THC levels in the cannabis plant are determined, and the dry weight of the inflorescence is collected at the same time to calculate the yields of CBD and THC per plant. The experimental results are shown in Table 1.

TABLE 1

| Ind. Irradiation | Peak WL/ nm | CBD level (%) | THC level (%) | Inflorescence DW g/plant | CBD yield g/plant | THC yield g/plant |
| --- | --- | --- | --- | --- | --- | --- |
| Cont. Ex. 1 | 445 | 5.11 | 4.47 | 58.65 | 3.00 | 2.62 |
| Cont. Ex. 2 | 545 | 5.19 | 4.56 | 73.53 | 3.82 | 3.35 |
| Cont. Ex. 3 | 571 | 5.21 | 4.55 | 71.42 | 3.72 | 3.25 |
| Exptl. Ex. 1 | 505 | 5.46 | 4.75 | 72.59 | 3.96 | 3.45 |
| Exptl. Ex. 2 | 515 | 5.68 | 4.91 | 76.38 | 4.34 | 3.75 |
| Exptl. Ex. 3 | 523 | 5.61 | 4.84 | 76.49 | 4.29 | 3.69 |
| Exptl. Ex. 4 | 526 | 5.44 | 4.77 | 75.49 | 4.11 | 3.60 |

The results suggest that the green light sources in experimental examples 1-4 are more effective than the light sources in control examples 1-3 in improving the levels of THC and CBD. Besides, the green light with peak wavelength at 515 nm is the most effective one which improves the levels of THC and CBD up to 11.15%. At the same time, the green light sources in experimental examples 1-4 are also good for the accumulation of inflorescence weight in cannabis, and improving the yields of CBD and THC per plant.

Embodiment 2

Top branches of strong cannabis mother plant are selected as stem cuttings for plant cutting. After the plant cutting is finished (the plant cutting stage is about 2 weeks), the cannabis seedlings with good rooting conditions are transplanted into the rock wool or the substrate for the vegetative growth phase (the vegetative growth stage is about 4 weeks). Each rock wool block has 1 plant, and a density for the transplanted cannabis seedlings is 9 plants/m². The plant is topped when the plant is about 20 cm high for triggering the growth of side branches. After the vegetative growth stage is finished, the plant is moved to the flower promotion stage for flower promotion treatment. The planting density of the plant in the flower promotion stage is 4 plants/m². A distinguishment to the male and female flowers is required. The male flowers are removed, and the female plants is cultivated as before. The cultivation environment is set to have a day and night temperature at 24-26° C./21-22° C., humidity at 60-70%, $CO_2$ concentration at 10000 ppm. Throughout the growth process, the LED light source is used to provide a light environment for the growth of the plant. An initial light intensity is set to 100 μmol/m²s. As the plant height increases, the light intensity reaches 750 μmol/m²s in the late stage, and the photoperiod is 12 h/d. Five control examples (Cont. Ex. 4-8 as shown in Table 2) and five experimental examples (Exptl. Ex. 5-9 as shown in Table 2) are provided. Green lights with different ratio are arranged. The blue light has a peak wavelength at 450 nm. The red light has a peak wavelength at 660 nm. The green light has a peak wavelength at 526 nm. At the same time, a ratio of the photon numbers between the red light (600-780 nm) and the photon number of the blue light (400-499 nm) is 4:1. When harvesting, the levels of THC and CBD in the cannabis are determined, and the dry weight of the inflorescence is collected at the same time to calculate the yields of THC and CBD per single plant. The experimental results are shown in Table 2.

TABLE 2

| | Spectral composition and Peak characteristics | | | | | | | |
|---|---|---|---|---|---|---|---|---|
| SN | X1, Ratio of 400-499 nm photons in 380-780 nm light source (%) | X2, Ratio of 500-599 nm photons in 380-780 nm light source (%) | X3, Ratio of 600-780 nm photons in 380-780 nm light source (%) | CBD level (%) | THC level (%) | Inflorescence DW g/plant | CBD yield g/plant | THC yield g/plant |
| Cont. Ex. 4 | 20 | 0 | 80 | 10.43 | 3.42 | 140.69 | 14.67 | 4.81 |
| Cont. Ex. 5 | 18.8 | 6 | 75.2 | 10.66 | 3.49 | 135.19 | 14.41 | 4.72 |
| Cont. Ex. 6 | 17.6 | 12 | 70.4 | 10.98 | 3.62 | 137.48 | 15.10 | 4.98 |
| Cont. Ex. 7 | 10.2 | 49 | 40.8 | 10.85 | 3.56 | 133.76 | 14.51 | 4.76 |
| Cont. Ex. 8 | 8.8 | 56 | 35.2 | 10.54 | 3.46 | 132.49 | 13.96 | 4.58 |
| Exptl. Ex. 5 | 16.4 | 18 | 65.6 | 11.24 | 3.88 | 147.36 | 16.56 | 5.72 |
| Exptl. Ex 6 | 15 | 25 | 60 | 11.45 | 4.01 | 146.57 | 16.78 | 5.88 |
| Exptl. Ex 7 | 13.8 | 31 | 55.2 | 11.67 | 4.08 | 149.21 | 17.41 | 6.09 |
| Exptl. Ex 8 | 12.6 | 37 | 50.4 | 11.78 | 4.15 | 148.34 | 17.47 | 6.16 |
| Exptl. Ex 9 | 11.6 | 42 | 46.4 | 11.41 | 4.03 | 145.09 | 16.55 | 5.85 |

The results suggest that it is possible to improve the levels of THC and CBD by adding into the combination of red light and blue light with different ratio of green light as shown in experimental examples 5-9, compared with the control examples 4-8. Compared with the control example 4, the CBD level and THC level in the experimental example 8 have been increased up to 12.94% and 21.35%, respectively. At the same time, it is beneficial to improve the accumulation of inflorescence weight of cannabis and increase the yields of CBD and THC per plant by adding into the combination of red light and blue light with different ratio of green light.

Embodiment 3

Top branches of strong cannabis mother plant are selected as stem cuttings for plant cutting. After the plant cutting is finished (the plant cutting stage is about 2 weeks), the cannabis seedlings with good rooting conditions are transplanted into the rock wool or the substrate for the vegetative growth phase (the vegetative growth stage is about 4 weeks). Each rock wool block has 1 plant, and a density for the transplanted cannabis seedlings is 9 plants/m². The plant is topped when the plant is about 20 cm high for triggering the growth of side branches. After the vegetative growth stage is finished, the plant is moved to the flower promotion stage for flower promotion treatment. The planting density of the plant in the flower promotion stage is 4 plants/m². A distinguishment to the male and female flowers is required. The male flowers are removed, and the female plants is cultivated as before. The cultivation environment is set to have a day and night temperature at 24-26° C./21-22° C., humidity at 60-70%, $CO_2$ concentration at 10000 ppm. Throughout the growth process, the LED light source is used to provide a light environment for the growth of the plant. An initial light intensity is set to 100 μmol/m²s. As the plant height increases, the light intensity reaches 800 μmol/m²s in the late stage, and the photoperiod is 12 h/d. A light source composed of 20% blue light and 80% red light is provided as the control example 9, wherein the blue light has a peak wavelength at 445 nm, the red light has a peak wavelength at 660 nm. On this basis, same ratio of green lights having different peak wavelengths being added in the control example 3 are provided as experimental examples 11-15 (Table 3). The experimental examples 11-20 also satisfy that a ratio of photon numbers between the red light (600-780 nm) and the blue light (400-499 nm) is 4:1. When harvesting, the levels of CBD and THC in the cannabis are determined, and the dry weight of the inflorescence is collected at the same time to calculate the yields of CBD and THC per plant. The experimental results are shown in Table 3.

TABLE 3

| | Spectral composition and Peak characteristics | | | | Biological indicators | | | | |
| --- | --- | --- | --- | --- | --- | --- | --- | --- | --- |
| SN | X1, Ratio of 400-499 nm photons in 380-780 nm light source (%) | X2, Ratio of 500-599 nm photons in 380-780 nm light source (%) | X3, Ratio of 600-780 nm photons in 380-780 nm light source (%) | Green peak WL | CBD level (%) | THC level (%) | Inflorescence DW g/plant | CBD yield g/plant | THC yield g/plant |
| Cont. Ex. 9 | 20 | 0 | 80 | — | 7.79 | 6.12 | 110.53 | 8.61 | 6.76 |
| Cont. Ex. 10 | 16 | 20 | 64 | 535 | 8.18 | 6.38 | 114.06 | 9.33 | 7.28 |
| Cont. Ex. 11 | 16 | 20 | 64 | 545 | 8.13 | 6.33 | 113.72 | 9.25 | 7.20 |
| Cont. Ex. 12 | 16 | 20 | 64 | 571 | 8.09 | 6.29 | 110.25 | 8.92 | 6.93 |
| Exptl. Ex. 10 | 16 | 20 | 64 | 505 | 8.34 | 6.54 | 112.45 | 9.38 | 7.35 |
| Exptl. Ex. 11 | 16 | 20 | 64 | 511 | 8.51 | 6.70 | 114.38 | 9.73 | 7.66 |
| Exptl. Ex 12 | 16 | 20 | 64 | 515 | 8.65 | 6.78 | 115.42 | 9.98 | 7.83 |
| Exptl. Ex 13 | 16 | 20 | 64 | 520 | 8.48 | 6.67 | 116.87 | 9.91 | 7.80 |
| Exptl. Ex 14 | 16 | 20 | 64 | 523 | 8.43 | 6.64 | 117.06 | 9.87 | 7.77 |
| Exptl. Ex 15 | 16 | 20 | 64 | 526 | 8.35 | 6.48 | 114.39 | 9.55 | 7.41 |

The results suggest that, compared with control examples 9-12, the light sources in experimental examples 10-15 will greatly improve the levels of THC and CBD in cannabis. More specifically, compared with control example 9, the light source in experimental example 12 improves the levels of CBD and THC up to 11.04% and 10.78%, respectively. At the same time, the green light is beneficial to improve the accumulation of inflorescence weight of cannabis and increase the yields of CBD and THC per plant.

In summary, plants experience different light qualities through photoreceptors such as phytochromes and cryptochromes. The light absorbed by plants is concentrated in the visible part of the wavelength range of 380 to 780 nm. Red light accounts for about 85% of the absorbed physiological radiation light energy, and blue light accounts for about 12%. Therefore, the red light and blue light are essential light qualities for plant growth. The red light is mainly used to generate assimilate and accumulate biomass, and the blue light is a necessary condition for chlorophyll synthesis and chloroplast formation. The blue light affects the morphology of plants by controlling the stomata shape. At the same time, the blue light can also promote the accumulation of secondary metabolites in plants. Green light has always been a controversial light quality. Some scholars believe that it will inhibit the growth of plants, cause short plants and reduce the yield of leafy vegetables. In the present disclosure, under the proof of the above-mentioned embodiments, it is preferable to supplement 18-42% of green light on the basis of red and blue light, which is more effective for promoting accumulation of levels and yields of CBD and THC in cannabis. Therefore, different plants may have different optimal spectral formula during growth. The special spectral formula for cannabis as provided may enable the cannabis to accumulate and synthesize more THC and CBD, secondary metabolites in the cannabis, during the industrial cultivation.

It should be noted that the aforementioned embodiments are merely preferred embodiments of the present disclosure, and those embodiments are not to be deemed as limiting the scope of the invention. The scope of the disclosure should be limited by the by the scope of the claims. It will be apparent to those skilled in the art that other modifications and changes may be made without departing from the spirit and scope of the disclosure.

What is claimed is:

1. A light regulation method for promoting accumulation of cannabinoid substances, comprising:
    adding an irradiation of a green light into an indoor growing environment of cannabis to improve the accumulation of levels and yields of tetrahydrocannabinol (THC) and cannabidiol (CBD); wherein a peak wavelength of the green light lies at 515 nm;
    wherein the step of adding the irradiation of green light having a peak wavelength at 505-526 nm comprises a combined irradiation with other wavelength bands or independent irradiation;
    in the combined irradiation with other wavelength bands, a light source comprises 18-42% green light;
    wherein the light source used in the indoor growing environment is a LED light source;
    the LED light source consists of 12.6% blue light, 37% green light, and 50.4% red light;
    the ratio of a photon number of the blue light to a photon number of the red light is 1:4;
    an initial light intensity is 80 μmol/m$^2$s, a maximum light intensity is 1000 μmol/m$^2$s, and a photoperiod is 10-16 h/d.

2. The method of claim 1, wherein a blue light has a peak wavelength at 440-460 nm, a red light has a peak wavelength at 655-690 nm.

3. The method of claim 1, wherein the LED light source is realized directly by a LED chip or by using the LED chip to excite a phosphor material.

* * * * *